(12) United States Patent
Hilbig et al.

(10) Patent No.: US 9,556,028 B2
(45) Date of Patent: Jan. 31, 2017

(54) METHOD AND ARRANGEMENT FOR GENERATING OXYGEN

(75) Inventors: Rainer Hilbig, Aachen (DE); Achim Gerhard Rolf Koerber, Eindhoven (NL); Mareike Klee, Straelen (DE); Wilhelmus Cornelis Keur, Weert (NL)

(73) Assignee: KONINKLIJKE PHILISP N.V., Eindhoven (NL)

(*) Notice: Subject to any disclaimer, the term of this patent is extended or adjusted under 35 U.S.C. 154(b) by 296 days.

(21) Appl. No.: 14/113,836

(22) PCT Filed: Apr. 19, 2012

(86) PCT No.: PCT/IB2012/051959
§ 371 (c)(1),
(2), (4) Date: Oct. 25, 2013

(87) PCT Pub. No.: WO2012/147015
PCT Pub. Date: Nov. 1, 2012

(65) Prior Publication Data
US 2014/0048409 A1 Feb. 20, 2014

(30) Foreign Application Priority Data

Apr. 28, 2011 (EP) ..................... 11164170

(51) Int. Cl.
*C01B 13/02* (2006.01)
*A61M 16/10* (2006.01)
(Continued)

(52) U.S. Cl.
CPC ............. *C01B 13/02* (2013.01); *A61M 16/10* (2013.01); *A61M 16/101* (2014.02); *B01D 53/22* (2013.01);
(Continued)

(58) Field of Classification Search
CPC .. C01B 13/02; C01B 13/0229; C01B 13/0251; C01B 3/042; C01B 3/045; C01B 13/0207; C01B 21/30; A61M 16/101; A61M 16/10; B01D 53/22; B01D 53/228; B01D 53/323; B01D 2256/12; B01J 19/088; B01J 19/126; B01J 19/127; B01J 19/129; B01J 19/2475
See application file for complete search history.

(56) References Cited

U.S. PATENT DOCUMENTS 5,427,747 A 6/1995 Kong
5,547,494 A 8/1996 Prasad et al.
(Continued)

FOREIGN PATENT DOCUMENTS

CN 1198360 A 11/1998
CN 1344430 A 4/2002
(Continued)

OTHER PUBLICATIONS

S.P.S. Badwal et al., "Ceramic Membrane Technologies for Oxygen Separation", Advanced Materials 2001, V. 13 (12-13) pp. 993-996.

*Primary Examiner* — Xiuyu Tai
(74) *Attorney, Agent, or Firm* — Michael W. Haas

(57) ABSTRACT

The present invention relates to a method of generating oxygen. The method addresses the objects of reducing the servicing work and improving the purity of the generated oxygen. According to the invention, the method comprises the steps of: providing an oxygen comprising gas at a primary side of a dense voltage drivable membrane (12); applying a voltage between a conductive element at the primary side of the membrane (12) and a conductive element at a secondary side of the membrane (12), the conductive elements being electrically connected to the membrane (12), wherein a plasma (18, 20) is generated at at least one of the primary side and the secondary side of the membrane (12), the plasma (18, 20) being used as conductive element.

9 Claims, 2 Drawing Sheets

(51) Int. Cl.
*B01D 53/22* (2006.01)
*B01D 53/32* (2006.01)
*B01J 19/08* (2006.01)

(52) U.S. Cl.
CPC ........... *B01D 53/228* (2013.01); *B01D 53/323* (2013.01); *B01J 19/088* (2013.01); *C01B 13/0229* (2013.01); *C01B 13/0251* (2013.01); *B01D 2256/12* (2013.01)

(56) References Cited

U.S. PATENT DOCUMENTS

| | | |
|---|---|---|
| 6,544,404 B1 | 4/2003 | Mazanec et al. |
| 2004/0265137 A1 | 12/2004 | Bar-Gadda |

FOREIGN PATENT DOCUMENTS

| | | |
|---|---|---|
| EP | 0858826 A2 | 8/1998 |
| EP | 2196235 | 6/2010 |
| JP | 2001087621 A | 4/2001 |
| JP | 2005001908 | 1/2005 |
| JP | 2006136812 A | 6/2006 |
| JP | 2007099549 | 4/2007 |
| KR | 20020065194 A | 8/2002 |
| WO | WO0057510 A1 | 9/2000 |
| WO | WO2011073889 | 6/2011 |
| WO | WO2012052915 A1 | 4/2012 |

METHOD AND ARRANGEMENT FOR GENERATING OXYGEN

CROSS-REFERENCE TO PRIOR APPLICATIONS

This application is the U.S. National Phase application under 35 U.S.C. §371 of International Application Serial No. PCT/IB2012/051959, filed on Apr. 19, 2012, which claims the benefit of European Application Serial No. 11164170.0, filed on Apr. 28, 2011. These applications are hereby incorporated by reference herein.

FIELD OF THE INVENTION

The invention relates to the field of oxygen generation. More particularly, the invention relates to the field of oxygen separation from an oxygen comprising gas in the field of therapeutic applications.

BACKGROUND OF THE INVENTION

Oxygen therapy is the administration of oxygen as a therapeutic modality. It is widely used for a variety of purposes in both chronic and acute patient care as it is essential for cell metabolism, and in turn, tissue oxygenation is essential for all physiological functions. Oxygen therapy should be used to benefit the patient by increasing the supply of oxygen to the lungs and thereby increasing the availability of oxygen to the body tissues, especially when the patient is suffering from hypoxia and/or hypoxemia. Oxygen therapy may be used both in applications in hospital or in home care. The main home care application of oxygen therapy is for patients with severe chronic obstructive pulmonary disease (COPD).

Oxygen may be administered in a number of ways. A preferable way of oxygen administration is by using a so called on demand generation of oxygen. Referring to this, commercial solutions, so-called oxygen concentrators or separators, respectively, are widely known. These oxygen concentrators mostly separate oxygen from an oxygen comprising gas, so that the oxygen is provided on demand, i.e. directly before use. Most known oxygen concentrators require a compressor to compress the oxygen comprising gas. Furthermore, oxygen, preferably pure oxygen, has to be generated. Most known oxygen concentrators thus comprise an organic membrane to separate oxygen from the oxygen comprising gas.

The major drawbacks of the known oxygen concentrators are high costs and a limited convenience with respect to noise. Furthermore, undesired constituents of the oxygen comprising gas, mostly nitrogen, are adsorbed on the membrane thereby causing the requirement of a so-called swing process by which the adsorbed gas is desorbed from the membrane. During that desorption step, a separation of oxygen is not possible, because of which two membranes are desired which further increases the costs. Apart from that, the compressors are mostly noisy leading to a decreased convenience especially when the oxygen concentrator is used overnight. Furthermore, the generated oxygen is non-sterile, because of which a further measure of disinfection is often desired or necessary.

Known from U.S. Pat. No. 6,544,404 B1 is an oxygen separation process for the separation of oxygen from an oxygen containing fluid. This process uses mixed ionic and electronic membranes having a chemically active porous coating selected from the group consisting of metals, metal oxides and combinations thereof. This prior art wants to address the object of providing superior flux without sacrificing mechanical and physical compatibility of the composite membrane. However, these kinds of membranes require a certain amount of partial pressure difference between the primary side and the secondary side of the membrane, which in some cases is preferred to be avoided.

Additionally, there are known methods for separating oxygen which use pure voltage driven membranes, or pure ionic conductive membranes, respectively, having electrodes as outer conductive layers in order to generate an oxygen flux through the membrane. One major drawback of these membranes, or the use of the latter, respectively, may be seen in the fact that these membranes may require elevated temperatures in order to work properly. Under these conditions, however, there is the risk of components of the electrodes to be released from the electrodes which consequently are present in the stream of generated oxygen. In some applications, for example in the field of therapeutic applications, however, the presence of these compounds has to be avoided or at least significantly reduced. Additionally, arrangements being used for performing this method in some cases require an intense servicing work. Apart from that, electrodes being present on the surface of the membrane have to be permeable for gas or at least for oxygen, which might require a rather complex manufacturing process.

SUMMARY OF THE INVENTION

It is an object of the present invention to provide a method and an arrangement for generating oxygen which overcomes at least one of the disadvantages known in the art.

It is a further object of the present invention to provide a method and an arrangement for generating oxygen which are usable with reduced servicing work and in which the danger of undesired compounds in the generated oxygen stream to be present is significantly reduced.

These objects are achieved by a method of generating oxygen according to claim 1. These objects are furthermore achieved by an arrangement for generating oxygen according to claim 9. Preferred embodiments of the present invention are defined in the dependent claims.

The invention relates to a method of generating oxygen, said method comprising the steps of: providing an oxygen comprising gas at a primary side of a dense voltage drivable membrane; applying a voltage between a conductive element at the primary side of the membrane and a conductive element at a secondary side of the membrane, the conductive elements being electrically connected to the membrane, wherein a plasma is generated at at least one of the primary side and the secondary side of the membrane, the plasma being used as the conductive element at the primary side of the membrane and/or as the conductive element at the secondary side of the membrane.

The step of providing an oxygen comprising gas at a primary side of a dense membrane according to the invention comprises each measure which is suitable for bringing in contact the primary side of the membrane with the oxygen comprising gas. This step thus exemplarily comprises to simply arrange the membrane, or particularly its primary side, in an atmosphere comprising an oxygen comprising gas. Additionally, this step may comprise to guide an oxygen comprising gas to the primary side of the membrane, for example by means of a gas supplying device such as a pump, a compressor or the like.

A primary side of the membrane according to the invention shall particularly refer to the side of the membrane, the oxygen comprising gas is guided to, i.e. the retentive side of the membrane. Correspondingly, the secondary side of the membrane shall particularly refer to the side of the membrane at which the generated stream of pure oxygen is present, i.e. the permeate side of the membrane.

Additionally, the term dense membrane, as used herein, shall refer to a membrane which is permeable for oxygen but non-permeable for other gases, especially for nitrogen. Consequently, a dense membrane is suitable for separating oxygen from an oxygen comprising gas, thereby generating pure or essentially pure oxygen. Apart from that, a voltage drivable membrane in the sense of the present invention shall particularly mean a membrane which generates a flux of pure oxygen solely by the provision of a voltage across the membrane, i.e. between the primary side and the secondary side of the membrane. Consequently, a voltage drivable membrane according to the present invention is particularly based on pure oxygen-ion conducting solid electrolyte membrane which might be non-porous. The voltage drivable membrane in the sense of the present invention is thus no mixed conducting membrane, for example having both oxygen-ion and electronic conductivities.

A conductive element in the sense of the present invention shall furthermore particularly mean any element which is suitable for applying a voltage to and allowing a current to flow due to the applied voltage and the electrical connection with the ionic conducting membrane. Consequently, a conductive element shall particularly mean an electronic conducting element. According to the invention, at least one conductive element is formed by the generated plasma. However, in case only one conductive element is formed by the plasma, the further conductive element may be formed by a conventional electrode, for example. In the latter case, the electrode may preferably be arranged on the surface of the membrane to allow oxygen to be generated properly using the method according to the invention. In this case, the electrode has to be permeable for gases or at least for oxygen.

A plasma according to the invention shall particularly mean a gas in which charged particles are present. The charged particles may thereby comprise ions or electrons or further charged particles.

Additionally, the term oxygen comprising gas, as used herein, shall refer to any gas which at least partly comprises oxygen or which mainly consists of oxygen.

According to the invention, oxygen is generated, or separated from an oxygen comprising gas, respectively, thereby addressing the above defined objects. In detail, due to the fact that a plasma is generated at at least one of the primary side and the secondary side of the membrane, at least one electrode may be exchanged by ionized gas, or the plasma, respectively. Consequently, the danger of compounds being present in the electrodes and being released from the latter under working conditions is significantly reduced in case only one electrode is exchanged by a plasma, or it is completely avoided.

With this regard, it is especially preferred that the electrode at the secondary side of the membrane is exchanged by a plasma, i.e. a plasma is formed solely at the secondary side of the membrane. This may under some circumstances be sufficient because compounds potentially being released from the electrode under working conditions will not permeate through the membrane and will thus not deteriorate the flux of pure oxygen. Consequently, the method according to the invention is especially preferred for generating oxygen in a very high purity and without particularly toxic impurities. For example, the method according to the invention is particularly suitable in order to administer the generated oxygen to patients in the course of therapeutic applications.

Additionally, by generating a plasma at at least one of the primary and the secondary side of the membrane, the servicing work of an arrangement being designed for the method according to the invention may significantly be reduced. In detail, in case compounds being present in the electrode, such as cobalt, are released under operation conditions, not only the generated gas stream may comprise impurities, but the electrode itself or its composition, respectively, is deteriorated. This may result in the electrode not to work properly after a certain amount of time thus requiring an exchange of the electrode after a certain working period. This servicing work may be saved in case no electrode is present or the amount of electrodes is reduced. Consequently, servicing work and thus costs required for performing the method according to the invention may be reduced.

The generated plasma may furthermore be used to heat the dense membrane in order to bring the latter to its required working conditions. In detail, it may sometimes be advantageous to heat a membrane in order to let it work properly. The energy being required for heating the membrane may at least partly be provided by the plasma. Consequently, in some cases no additional heating device has to be provided. Furthermore, by providing a plasma especially at the secondary side of the membrane, sterile oxygen is generated, which may be preferred in some cases, especially in the field of therapeutic applications.

A further advantage of the method according to the invention may be found in the fact that by using a voltage drivable membrane the oxygen flux may be adjusted very precisely by varying the voltage applied. This is due to the fact that the oxygen flux rate is directly proportional to the voltage applied. Additionally, an overpressure on the secondary side of the membrane may easily be generated in the required amount simply by adjusting the voltage applied to a suitable amount. Consequently, a very precise control with respect to the generated oxygen, such as with respect to its amount, i.e. flux and/or pressure is possible by using the method according to the invention.

Additionally, compared to mixed ionic and electronic conducting membranes, for example, no pressure difference between the primary side and the secondary side is required for generating oxygen. This allows working without nuisance gas compressing means resulting in the method according to the invention to be much more quiet.

According to a preferred embodiment of the present invention the plasma is generated both at the primary side and the secondary side of the membrane. This embodiment allows to further reducing the servicing work and thus the costs required with respect to the method according to the invention. In detail, an electrode for the membrane is not only saved at one side, especially at the secondary side of the membrane, but the membrane may be provided without any electrode. Consequently, the conductive elements both at the primary side and the secondary side of the membrane are formed by a plasma. This results in the step of exchanging the respective electrodes as well as the step of controlling the electrodes is completely avoided. Apart from that, it may be avoided that particles being released from an electrode being arranged at the primary side of the membrane may be guided to the membrane and contaminating the latter, which would lead to a reduced lifetime of the membrane. Consequently, the method according to this embodiment reduces servicing work and extends the lifetime of the membrane. Thus, this embodiment allows to further reducing costs being required by performing the method according to the invention.

According to a further preferred embodiment of the present invention the plasma is generated to provide a charge carrier density in the range of $\leq 1 \times 10^{-3}$ m$^{-3}$. A charge carrier density according to the invention should particularly mean the amount of charged particles with respect to the gaseous molecules. A concentration of charged particles in the above identified range is sufficiently high for allowing a suitable oxygen flux through the membrane for a wide range of applications, thereby allowing an appropriate overpressure of pure oxygen on the secondary side of the membrane to be provided. In detail, the conductivity of the plasma is high enough in order to allow an appropriate voltage to be applied and to couple the latter to the membrane. Additionally, a method according to this embodiment may be carried out energy saving due to the fact that only a limited amount of charged particles has to be generated. Consequently, this embodiment allows to further reduce costs by performing the method according to the invention.

It is furthermore preferred that the membrane is heated to a temperature in the range of $\geq 500°$ C. to $\leq 700°$ C. Especially by heating the membrane to the above identified temperature range, a suitable flux of oxygen through the membrane may be provided due to the fact that the force of guiding oxygen through the membrane may be improved due to a heating step. Additionally, by heating the membrane, sterile oxygen may be generated which is particularly advantageous in case the plasma is formed solely on the primary side of the membrane and the method is furthermore used in the course of therapeutic applications and thus in course of oxygen administration to patients.

With respect to the plasma to be provided, there are several advantageous embodiments of plasma generation possible to be used. It may thereby be distinguished between non local thermal equilibrium (non LTE) discharges and LTE discharges. Non LTE discharges such as a dielectric barrier discharge come up with nearly no gas heating while LTE discharges such as discharges (plasmas) in high intensity discharge lamps, come up with significant gas heating and high gas temperatures.

In detail, it may be preferred to generate the plasma by applying a voltage between two electrodes. This embodiment uses excitation by electrostatic fields, wherein the charged particles are generated by a discharge and furthermore by electron impact ionization. In detail, a voltage, preferably with respect to direct current, is applied between two electrodes. By adjusting an appropriate combination of voltage, distance of the electrodes and gas pressure, a discharge is formed leading to a plasma to be generated. This embodiment is an especially easy way to perform a plasma. In detail, no complex arrangements have to be provided, making the method according to this embodiment especially cost-saving.

According to a further embodiment of the present invention the plasma is generated based on capacitive excitation. A plasma generation being based on capacitive excitation uses an excitation of electromagnetic fields, wherein the charged particles are generated by electron impact ionization. In detail, an alternating electrical field may be applied to two capacitor plates. Between the plates, a plasma is generated. One main advantage of a capacitive excitation is the fact that the plates between which the plasma is generated do not have to be arranged in direct vicinity to the oxygen comprising gas being provided at the primary side of the dense membrane, or to the stream of generated pure oxygen at the secondary side of the dense membrane, or in the gas streams, respectively. In contrast thereto, the plates may be arranged separated from the respective gas or gas streams, for example by a glass plate or the like. Consequently, by using this so called electrodeless plasma generation neither the oxygen comprising gas, nor the generated pure oxygen is in direct contact with the capacitor plates. This embodiment thus avoids particles of the capacitor plates to be released and introduced into the gas stream thereby avoiding contaminations to be introduced especially into the stream of pure oxygen. The method according to this embodiment thus allows to further increase the purity of the generated oxygen which is especially advantageous in the field of therapeutic applications. Apart from that, it may be avoided that particles being released from the capacitor plates may be guided to the membrane and contaminating the latter leading to a reduced lifetime of the membrane. Consequently, the method according to this embodiment further reduces servicing work and extends the lifetime of the membrane. Thus, this embodiment allows to further reduce costs being required by performing the method according to the invention.

It may furthermore be preferred that the plasma is generated based on inductive excitation. A plasma generation being based on inductive excitation, or magnetic excitation, respectively, uses an excitation of electromagnetic fields, wherein the charged particles are generated by electron impact ionization. In detail, a high frequent alternating current may be guided through a coil, which may lead to a discharge such as a glow discharge and thus to a plasma. Again, the coil may be arranged separated from the oxygen comprising gas and particularly from the stream of generated pure oxygen. Accordingly, again, an electrodeless generation of plasma may be performed leading to the above described advantages with respect to an improved purity of the generated oxygen and reduced servicing work.

In a still further embodiment of the present invention the plasma is generated based on electromagnetic waves. Preferably, microwaves or radio frequencies are used for exciting the oxygen or the oxygen comprising gas in order to generate the plasma. Microwaves according to the present invention shall particularly mean waves having a wavelength in the range of $\geq 1$ mm to $\leq 1$ m and having a frequency from $\geq 300$ MHz to $\leq 300$ GHz, whereas radio frequencies shall particularly mean waves having a wavelength in the range of $\geq 10$ cm to $\leq 100$ km with a frequency of up to 3 GHz. Again, the device for generating electromagnetic waves may be arranged separated from the oxygen comprising gas and particularly from the stream of generated pure oxygen. Accordingly, again, an electrodeless generation of plasma may be performed leading to the above described advantages with respect to an improved purity of the generated oxygen and reduced servicing work.

The invention furthermore relates to an arrangement for generating oxygen, the arrangement comprising a dense voltage drivable membrane having a primary side and a secondary side, a plasma generation device for generating a plasma at at least one of the primary side and the secondary side of the dense membrane, and a voltage source for providing a voltage between a plasma being generated by the plasma generation device and a further conductive element, the plasma and the further conductive element being arranged on opposite sides of the membrane.

A plasma generation device according to the invention may particularly mean any device which is capable of forming a plasma, wherein the plasma is an ionized gas like described above. In detail, a plasma generation device may comprise a voltage source comprising two electrodes in order to generate the plasma by applying a voltage between these two electrodes. Alternatively, the plasma generation device may comprise two capacitor plates between which a plasma is generated by means of capacitive excitation. Furthermore, a coil may be provided in order to generate the plasma based on inductive excitation or a device for generating microwaves, or radiofrequencies, respectively may be provided. However, the plasma generation device is not limited to the above described embodiments. Generally, any plasma generation device known in the art may be used.

Conductive elements being electrically connected to the membrane shall particularly mean that, in case of a plasma is used as conductive element, the plasma is generated in direct vicinity to the membrane and thus is present at the surface of the membrane and thus in direct contact. In case the conductive element is a conventional electrode, the latter may be arranged on the surface of the membrane like it is known in the art.

The arrangement according to the invention is particularly suitable for performing the method according to the invention. Consequently, the arrangement according to the invention allows generating oxygen with high purity and avoiding particles to be released from electrodes being coated on the membrane to be released in the stream of generated oxygen when using pure voltage drivable membranes.

A further advantage of an arrangement according to the invention may be seen in the significantly simplified manufacturing procedure of such an arrangement. In detail, electrodes, when being present on the membrane, not only have to be electrically conductive, but they also have to be permeable for gases, or at least for oxygen. To achieve this property, the material for forming the electrodes may to be chosen very specifically, or it has to be arranged with through holes, for example in a lattice-like structure, making the manufacturing method rather complex. Another possibility would be to arrange the electrodes as thin layers in which case the stability of the electrodes may in some cases lead to a problem. These points, however, have not to be taken into consideration by forming the conductive elements by a plasma due to the fact that the plasma does not exhibit a gas permeability problem with respect to gases, or oxygen, respectively.

According to a preferred embodiment of the present invention the further conductive element is formed by a plasma. This embodiment is thus designed without an electrode to be provided on the surface of the voltage drivable membrane. Consequently, the danger of compounds to be released from the membrane and being incorporated into the stream of generated oxygen is further reduced as well as the servicing work.

According to a further preferred embodiment of the present invention the membrane is based on a material comprising a ($MO_2$)-fluorite type oxide, a perovskite type oxide ($ABO_3$), an aurivillius ($Bi_2O_2$)($A_{n-1}B_nO_x$) intergrowth phase, a $La_2Mo_2O_9$ oxide, or an apatite $A_{10-x}(SiO_4)_6O_{2\pm\delta}$ lattice. These kinds of materials are very well suited for acting as a dense voltage drivable membrane due to the fact that they exhibit a good ionic conductivity and are furthermore stable and inert at the conditions being used for the method according to the invention. ($MO_2$)— fluorite type materials may thereby comprise $ZrO_2$ or $ZrO_2$ based materials, for example being doped or not with yttrium (Y), or yttrium oxide ($Y_2O_3$), or they may comprise Cer oxide ($CeO_2$) or materials based on cer oxide ($CeO_2$), being doped or not, for example with lower-valent cations such as gadolinium (Gd) or samarium (Sm), or they may comprise bismuth oxide ($\delta$-$Bi_2O_3$), which may be doped or not with rare earth dopants, such as yttrium (Y), dysprosium (Dy), or erbium (Er), for example in combination with higher valent cations such as wolfram (W) or niobium (Nb), wherein an example is $Bi_{0.8}Er_{0.2}O_{1.5}$, or they may comprise pyrochlores ($A_2B_2O_7$) such as $Gd_2Ti_2O_7$. Materials having a perovskite type structure ($ABO_3$) comprise for example $La_{1-x}Sr_xGa_{1-y}Mg_yO_{3-\delta}$ (LSGM), wherein x=0.10-0.20 and $\delta$=0.15-0.20. Aurivillius ($Bi_2O_3$)($A_{n-1}B_nO_x$) intergrowth phases may comprise preferably those materials based on $\gamma$-$Bi_4V_2O_{11}$ with partial substitution of vanadium (V) with transition metal cations, such as copper (Cu), nickel (Ni), cobalt (Co), or may be doped with tantal (Ta), antimony (Sb) or niobium (Nb). $La_2Mo_2O_9$-oxide conductors may be undoped or doped and may comprise for example the materials $La_{1.7}Bi_{0.3}Mo_2O_{9-\delta}$, $La_2Mo_{1.7}W_{0.3}O_{9-\delta}$, or $La_2Mo_{1.95}V_{0.05}O_{9-\delta}$. Apatite $A_{10-x}(SiO_4)_6O_{2\pm\delta}$ lattices comprise those materials preferably with A-site cations such as $Ln_{10-x}Si_6O_{26+y}$ wherein Ln stands for lanthanum (La), praseodymium (Pr), neodymium (Nd), samarium (Sm), gadolinium (Gd), dysprosium (Dy).

According to a still further embodiment of the present invention the plasma generation device is arranged separated from an oxygen comprising gas and from a stream of generated oxygen. This allows achieving the advantages like described above with respect to reduced servicing work and improved purity of the generated oxygen.

According to a further embodiment of the present invention a gas supplying device for guiding a stream of oxygen comprising gas to the primary side of the membrane is provided. This gas supplying device may enhance the performance of the arrangement according to the invention by providing a flow of oxygen comprising gas to the primary side of the dense membrane and may thus be formed by a pump, a compressor or the like. Additionally, a gas exchange of the gas being present in vicinity of the primary side of the membrane may be improved for example by using a fan, for example, as gas supplying device.

It may furthermore be preferred that the arrangement according to the invention is part of an oxygen administration device for therapeutic applications. Especially with respect to therapeutic applications, the effect of avoiding particularly toxic compounds, such as cobalt, to be released from the electrodes an inserted into the gas stream is particularly advantageous. Consequently, there is a special benefit to introduce an arrangement according to the invention into an administration device such as an oxygen administration device for therapeutic applications.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
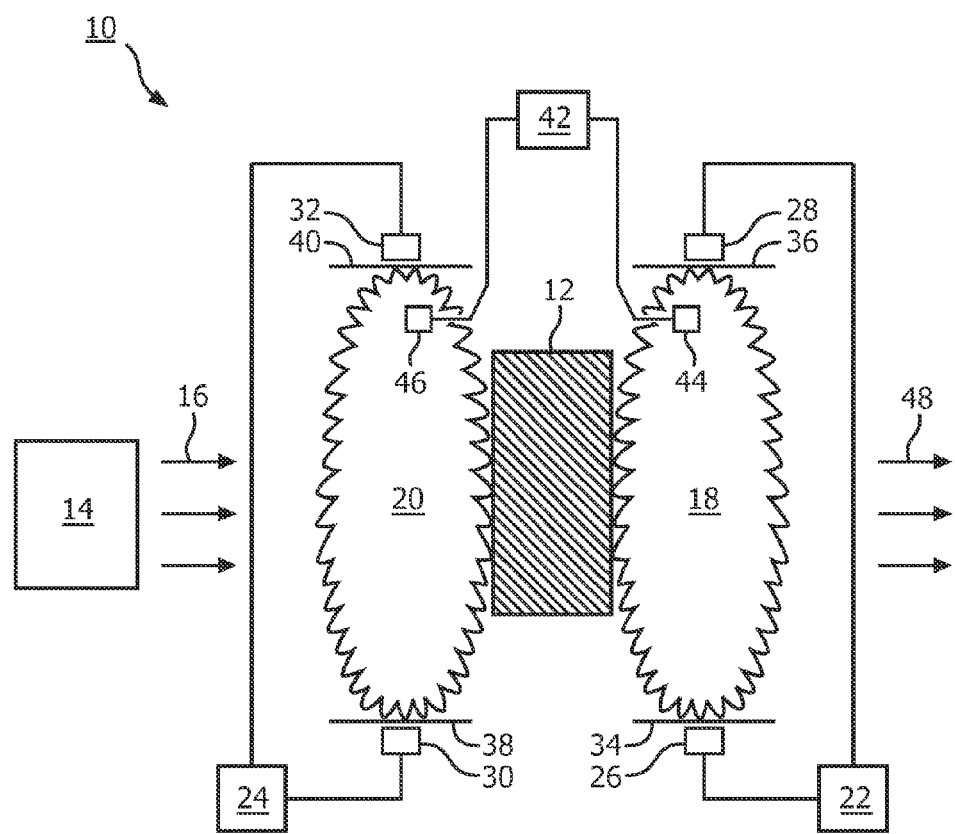
FIG. 1 shows a schematical sectional side view of an embodiment of the arrangement according to the invention.

In FIG. 1, an embodiment of an arrangement 10 according to the invention is schematically shown. The arrangement 10 according to the invention is particularly suitable for separating oxygen from an oxygen containing gas. The arrangement 10 may thus be part of an oxygen separation device, or an oxygen concentrator, respectively. The arrangement 10 is very well suitable for oxygen therapy, for example in home care applications. However, the arrangement 10 is not limited to therapeutic applications, but is furthermore suitable for all kinds of generation of oxygen. As a further exemplary application, it is referred to oxygen generation in airplanes.

The arrangement 10 comprises a dense voltage drivable membrane 12 having a primary side and a secondary side. The membrane 12 may be designed in a flat plate like shape like shown in FIG. 1, or it may be designed in a tubular form. However, the shape of the membrane 12 is not limited to the above described examples.

The membrane 12 may be based on a material comprising a ($MO_2$)-fluorite type oxide, a perovskite type oxide ($ABO_3$), an aurivillius ($Bi_2O_2$)($A_{n-1}B_nO_x$) intergrowth phase, a $La_2Mo_2O_9$ oxide, or an apatite $A_{10-x}(SiO_4)_6O_{2\pm\delta}$ lattice.

In order to provide an oxygen comprising gas at the primary side of the membrane 12, the latter, or its primary side, respectively, may be arranged in an atmosphere comprising the oxygen comprising gas. Furthermore, it is possible to guide a stream of oxygen comprising gas to the primary side of the membrane 12, because of which a gas supplying device 14 may be provided on the primary side of the membrane 12. Consequently, oxygen comprising gas, such as air, is guided to the vicinity of the membrane 12 at its primary side which is visualized by the arrows 16.

Due to the fact that the membrane 12, according to the invention, is a pure voltage drivable membrane, a voltage has to be applied between a conductive element at the primary side of the membrane 12 and a conductive element at the secondary side of the membrane 12, wherein the conductive elements are electrically connected to the membrane 12.

With respect to the conductive elements, at least one element is formed by a plasma 18, 20 which is generated at at least one of the primary side and the secondary side of the membrane 12. In case a plasma 18 is generated only at one side of the membrane 12, particularly at the secondary side, the conductive element on the respective opposite side of the membrane 12 may be formed by an electrode, the latter being coated on the surface of the membrane 12. According to FIG. 1, however, the plasma 18, 20 is provided on both the primary and the secondary side of the membrane 12. Consequently, according to the embodiment of FIG. 1, a plasma generation device 22, 24 for generating a plasma 18, 20 at both the primary side and the secondary side of the dense membrane 12 is provided. The plasma 18 is thus generated in pure oxygen at the secondary side of the membrane, whereas the plasma 20 is generated in the oxygen comprising gas at the primary side of the membrane 12.

With respect to the generated plasma 18, 20, there are several advantageous embodiments in order to generate the latter. In detail, the plasma generation device 22 may comprise electrodes as plasma generation means 26, 28 at the secondary side of the membrane 12, whereas the plasma generation device 24 may comprise electrodes as plasma generation means 30, 32 at the primary side of the membrane 12. The electrodes are in this case connected to a voltage source being part of the plasma generation device 22, 24 in order to apply a voltage between the electrodes and thus to generate the plasma 18, 20, like shown in FIG. 1.

However it may as well be possible to generate the plasma based on capacitive excitation, based on inductive excitation or based on electromagnetic waves, for example.

In case of capacitive excitation, the plasma generation device 22, 24 may comprise a voltage source creating a alternating electrical field between two capacitor plates as plasma generation means 26, 28 and/or 30, 32. The capacitor plates may be arranged behind a separator 34, 36, 38, 40 in order to separate the plates from the respective gas stream. The separator 34, 36, 38, 40 may be formed of glass, for example. Consequently, no direct contact of the plasma generation device 22, 24, or its plasma generation means 26, 28, 30, 32 and the respective gas or gas stream is present.

In case of inductive excitation, the plasma generation device 22, 24 may comprise a source of high frequent alternating current which is connected to coils as plasma generation means 26, 28 and/or 30, 32. With respect to inductive excitation, the plasma may preferably be generated in vicinity to a membrane having a tubular shape. This is shown with respect to FIG. 2.

Figure 2:
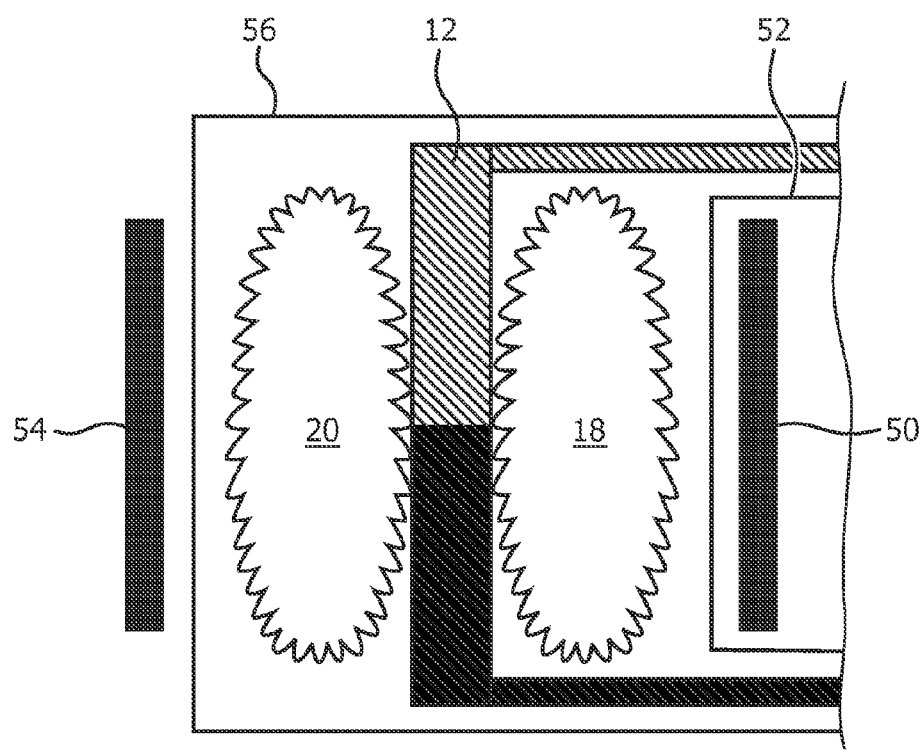
FIG. 2 shows a partial schematical sectional side view of a further embodiment of the arrangement according to the invention.

According to FIG. 2, a dense voltage drivable membrane 12 is shown. The membrane 12 is only partly shown and has a tubular shape. Further details, such as a voltage source 42 being coupled to the membrane 12 are not shown in FIG. 2, it is thus referred to FIG. 1. However, the general functionality of the arrangement according to FIG. 2 is comparable to FIG. 1. In vicinity to the membrane 12, a plasma 18 is generated at its secondary side, i.e. in the generated oxygen. With respect to its tubular shape, the secondary side may be arranged inside the membrane 12. Correspondingly, a plasma 20 is generated at the primary side of the membrane 12, wherein this plasma 20 is generated in the oxygen comprising gas. With respect to its tubular shape, the primary side may be arranged surrounding the membrane 12. With respect to the plasma 18 being generated at the secondary side of the membrane 12, the latter may be generated by an inner coil 50. The inner coil 50 may be formed as a wire formed on ferrite. Preferably, the coil 50 is arranged separated from the membrane 12 and from the generated oxygen by a separator 52, for example being formed from glass. Correspondingly, the plasma 20 being generated at the primary side of the membrane 12 is generated by an outer coil 54. The outer coil 54 may be formed as an air core coil and preferably is arranged separated from the membrane 12 by a separator 56, for example being formed from glass. Consequently, no direct contact of the coils 50, 54 and the respective gas stream is present. Apart from inductive excitation, the tubular shape of the membrane 12 may as well be used with respect to the further methods of generating the plasma like described above and for embodiments using a plasma 18 only on one side of the membrane 12.

Referring back to FIG. 1 and with respect to plasma generation based on electromagnetic waves, the plasma generation device 22, 24 may comprise a source of microwaves, or radiofrequencies respectively, as plasma generation means 26, 28 and/or 30, 32. The sources of electromagnetic radiation again may be arranged behind a separator 34, 36, 38, 40 in order to separate them from the respective gas stream. The separator 34, 36, 38, 40 may be formed of glass, for example. Consequently, no direct contact of the plasma generation device 22, 24, or its plasma generation means 26, 28, 30, 32 and the respective gas or gas stream is present.

In order to separate the oxygen from the oxygen comprising gas, a voltage has to be applied between a conductive element at the primary side of the membrane 12 and a conductive element at the secondary side of the membrane 12. According to the invention, like stated above, at least one conductive element is formed by the generated plasma 18, 20, especially preferred on the secondary side of the membrane 12. Accordingly, a voltage source 42 for providing a voltage between the plasma 18 generated by the plasma generation device 22 and a further conductive element is provided, the plasma 18 and the further conductive element being arranged on opposite sides of the membrane 12. The voltage source 42 may be a current source, preferably a source for direct current, and may be coupled to the membrane 12 via the plasma 18 and the further conductive element. In case an electrode is used for the further conductive element, a simple conductive connection, such as a cable may be provided between the electrode and the voltage source 42. In case of using a plasma 18, 20 as conductive element, the current source, or voltage source 42, respectively, may be coupled to the plasma 18, 20 and thus to the membrane 12 with help of suited coupling devices 44, 46. Examples for coupling devices 44, 46 comprise in a non limiting manner electrodes like known from low and high pressure gas discharge lamps, for example. The coupling devices 44, 46 are arranged in the plasma 18, 20 and preferably in a safe distance from the respective gas flows and especially from the generated oxygen, and additionally from the membrane 12. Preferably, the voltage source 42 is designed to apply a suitable voltage between the conductive element on the primary side of the membrane 12 and the conductive element at the secondary side of the membrane 12. The voltage to be applied should be chosen in order to generate a desired flow of pure oxygen at the secondary side of the membrane 12. However, the voltage applied may be varied in dependence of the plasma to be generated and the membrane to be used.

A method of generating oxygen according to the invention being carried out with an arrangement 10 like described above may be performed as follows. An oxygen comprising gas, such as air, is provided at the primary side of the dense voltage drivable membrane 12. A voltage is applied between a conductive element at the primary side of the membrane 12 and a conductive element at the secondary side of the membrane 12. Due to the fact that at least one conductive element is formed by a plasma 18, 20, the latter is generated at at least one of the primary side and the secondary side of the membrane 12. In detail, the plasma 18 may be generated to provide a charge carrier density in the range of $\leq 1 \times 10^{-3}$. Due to the coupling of the voltage source 42 with the voltage driven membrane 12 via the conductive elements and the presence of the oxygen comprising gas at the primary side of the membrane 12, the oxygen separation process may start and a flow of pure or essentially pure oxygen 48 is generated.

It may thereby be preferred that the membrane 12 is heated to a temperature in the range of $\geq 500°$ C. to $\leq 700°$ C., wherein the plasma 18, 20 may be used at least partly to heat the membrane.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. Method of generating oxygen, said method comprising the steps of:
    providing an oxygen comprising gas at a primary side of a membrane;
    applying a voltage between a conductive element at the primary side of the membrane and a conductive element at a secondary side of the membrane, the conductive elements being electrically connected to the membrane,
    wherein a plasma is generated at at least one of the primary side and the secondary side of the membrane, the plasma being used as the conductive element at the primary side of the membrane and/or as the conductive element at the secondary side of the membrane, and wherein the membrane is configured to separate oxygen from the oxygen comprising gas responsive to the voltage being applied between the primary side of the membrane and the secondary side of the membrane.

2. Method according to claim 1, wherein the plasma is generated both at the primary side and the secondary side of the membrane.

3. Method according to claim 1, wherein the plasma is generated to provide a charge carrier density in the range of $\leq 1 \times 10^{-3}$ m$^{-3}$.

4. Method according to claim 1, wherein the membrane is heated to a temperature in the range of $\geq 500°$ C. to $\leq 700°$ C.

5. Method according to claim 1, wherein the plasma is generated by applying a voltage between two electrodes.

6. Method according to claim 1, wherein the plasma is generated based on capacitive excitation.

7. Method according to claim 1, wherein the plasma is generated based on inductive excitation.

8. Method according to claim 1, wherein the plasma is generated based on electromagnetic waves.

9. Method according to claim 1, wherein the membrane is an oxygen-ion conducting solid electrolyte membrane and is configured to be permeable for oxygen.

\* \* \* \* \*